(12) United States Patent
Tezuka et al.

(10) Patent No.: US 9,217,709 B2
(45) Date of Patent: Dec. 22, 2015

(54) ESTIMATION APPARATUS, ESTIMATION METHOD, INTEGRATED CIRCUIT, AND RECORDING MEDIUM

(71) Applicant: Panasonic Intellectual Property Corporation of America, Torrance, CA (US)

(72) Inventors: Tadanori Tezuka, Fukuoka (JP); Tsuyoshi Nakamura, Fukuoka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 14/224,113

(22) Filed: Mar. 25, 2014

(65) Prior Publication Data

US 2014/0291522 A1    Oct. 2, 2014

(30) Foreign Application Priority Data

Mar. 29, 2013  (JP) .................................. 2013-071700

(51) Int. Cl.
  *G01N 21/55*  (2014.01)
  *G01N 21/25*  (2006.01)
  (Continued)

(52) U.S. Cl.
  CPC .................. *G01N 21/55* (2013.01); *G01J 3/027* (2013.01); *G01J 3/108* (2013.01); *G01J 3/46* (2013.01); *G01J 3/501* (2013.01); *G01J 3/513* (2013.01);
  (Continued)

(58) Field of Classification Search
  CPC ......... G01J 3/108; G01N 21/27; G01N 21/25; G01N 21/55

USPC ...................................................... 250/339.11
See application file for complete search history.

(56) References Cited

U.S. PATENT DOCUMENTS 5,353,053 A    10/1994  Nishioka et al.
7,012,643 B2 *  3/2006  Frame .......................... 348/272
(Continued)

FOREIGN PATENT DOCUMENTS

JP        58-186022       10/1983
JP        05-223638        8/1993
(Continued)

OTHER PUBLICATIONS

Kiyosumi Kidono et al., "Object Recognition based on Near-Infrared Spectral Reflectance", General Conference 2009, The Institute of Electronics, Information and Communication Engineers, Information/System Lecture Collection 2, 2009, p. 101 (with English translation).

(Continued)

*Primary Examiner* — Marcus Taningco
(74) *Attorney, Agent, or Firm* — Wenderoth, Lind & Ponack, L.L.P.

(57) ABSTRACT

An estimation apparatus using reflected light of infrared light reflected on an object, the estimation apparatus including: a single input unit including a first pixel having first spectral sensitivity characteristics in a wavelength range of the infrared light and a second pixel having second spectral sensitivity characteristics different from the first spectral sensitivity characteristics in the wavelength range of the infrared light; and an estimator that estimates at least either one of a color or a material of the object based on a first output value that is an output value of the reflected light from the first pixel and based on a second output value that is an output value of the reflected light from the second pixel.

10 Claims, 9 Drawing Sheets

(51) Int. Cl.

| | | |
|---|---|---|
| *G01N 21/27* | (2006.01) | |
| *G01J 3/46* | (2006.01) | |
| *G01N 21/3563* | (2014.01) | |
| *G01J 3/51* | (2006.01) | |
| *G01J 3/10* | (2006.01) | |
| *G01J 3/50* | (2006.01) | |
| *G01J 3/02* | (2006.01) | |
| *G01N 21/17* | (2006.01) | |

(52) U.S. Cl.
CPC ............ *G01N 21/25* (2013.01); *G01N 21/27* (2013.01); *G01N 21/3563* (2013.01); *G01J 2003/466* (2013.01); *G01N 2021/1765* (2013.01)

(56) References Cited

U.S. PATENT DOCUMENTS

| | | | |
|---|---|---|---|
| 7,579,593 B2 * | 8/2009 | Onozawa et al. ............ 250/332 |
| 2006/0103738 A1 * | 5/2006 | Sano ........................... 348/222.1 |
| 2006/0249683 A1 * | 11/2006 | Goldberg et al. ......... 250/370.01 |
| 2007/0146512 A1 * | 6/2007 | Suzuki et al. ................. 348/272 |
| 2008/0106620 A1 * | 5/2008 | Sawachi ........................ 348/262 |
| 2009/0303467 A1 | 12/2009 | Ashdown et al. |
| 2009/0322923 A1 * | 12/2009 | Maehara ....................... 348/308 |
| 2010/0020209 A1 * | 1/2010 | Kim .............................. 348/294 |
| 2010/0157091 A1 * | 6/2010 | Honda et al. ................ 348/223.1 |
| 2011/0188026 A1 * | 8/2011 | Lee et al. ...................... 356/5.01 |

FOREIGN PATENT DOCUMENTS

| | | |
|---|---|---|
| JP | 2009-212824 | 9/2009 |
| JP | 2009-544017 | 12/2009 |
| WO | 99-08080 | 2/1999 |
| WO | 2008/009093 | 1/2008 |

OTHER PUBLICATIONS

Mariko Takeuchi et al., "Construction of Hand Waving Interface System Using Near-Infrared Skin Detection Method", The Institute of Image Information and Television Engineers, ITE Technical Report vol. 34, No. 34, ME2010-122, Aug. 2010, pp. 35-36 (with English translation).

International Search Report issued Jun. 10, 2014 in corresponding International (PCT) Application No. PCT/JP2014/001400.

* cited by examiner

| Output value of R pixel / Output value of G pixel | Output value of G pixel / Output value of B pixel | Output value of B pixel / Output value of R pixel | Color and material of object |
|---|---|---|---|
| 0.2 | 0.6 | 1.3 | Color = x1<br>Material = Y1 |
| 1.2 | 0.9 | 1.4 | Color = x2<br>Material = Y2 |
| 0.5 | 1.1 | 0.9 | Color = x3<br>Material = Y3 |
| 1.2 | 1.0 | 1.4 | Color = x2<br>Material = Y2 |
| ⋮ | ⋮ | ⋮ | ⋮ |

1701

ESTIMATION APPARATUS, ESTIMATION METHOD, INTEGRATED CIRCUIT, AND RECORDING MEDIUM

CROSS REFERENCE TO RELATED APPLICATION

The present application claims the benefit of Japanese Patent Application No. 2013-071700 filed on Mar. 29, 2013. The entire disclosure of the above-identified application, including the specification, drawings and claims, is incorporated herein by reference in its entirety.

BACKGROUND OF THE INVENTION

1. Field of the Invention

The present disclosure relates to an estimation apparatus that estimates at least either one of a color or a material of an object by using infrared light.

2. Description of the Related Art

Heretofore, there has been one that estimates a material and the like of an object by dispersing incident light into three pieces by a prism, by installing narrow-band band-pass filters between the respective pieces of the dispersed light and image sensors, and by using information imaged by the three image sensors (refer to Object Recognition based on Near-Infrared Spectral Reflectance, General Conference 2009, The Institute of Electronics, Information and Communication Engineers, Information/System Lecture Collection 2, 2009, p. 101).

However, in the conventional configuration described above, there is a problem that the prism, the band-pass filters and the three image sensors are required to cause a size increase of a device.

SUMMARY OF THE INVENTION

The present disclosure provides an estimation apparatus capable of estimating at least either one of a color or a material of an object without causing the size increase of the device.

An estimation apparatus according to an aspect of the present disclosure is an estimation apparatus using reflected light of infrared light reflected on an object, the estimation apparatus including: a single image sensor including a first pixel having first spectral sensitivity characteristics in a wavelength range of the infrared light and a second pixel having second spectral sensitivity characteristics different from the first spectral sensitivity characteristics in the wavelength range of the infrared light; and an estimator that estimates at least either one of a color or a material of the object based on a first output value that is an output value of the reflected light from the first pixel and based on a second output value that is an output value of the reflected light from the second pixel.

Note that these general or specific aspects may be implemented by a method, a system, an integrated circuit, a computer program, and a computer-readable recording medium, such as a CD-ROM, or may be implemented by arbitrary combinations of the method, the system, the integrated circuit, the computer program and the recording medium.

In accordance with the estimation apparatus according to the aspect of the present disclosure, at least either one of the color or the material of the object can be estimated without causing the size increase of the device.

BRIEF DESCRIPTION OF DRAWINGS

FIG. 8 is a diagram showing an example of an array of an image sensor in the embodiment;

FIG. 11 is a diagram showing an example of a table in the embodiment.

DETAILED DESCRIPTION OF THE PREFERRED EMBODIMENT

Figure 1:
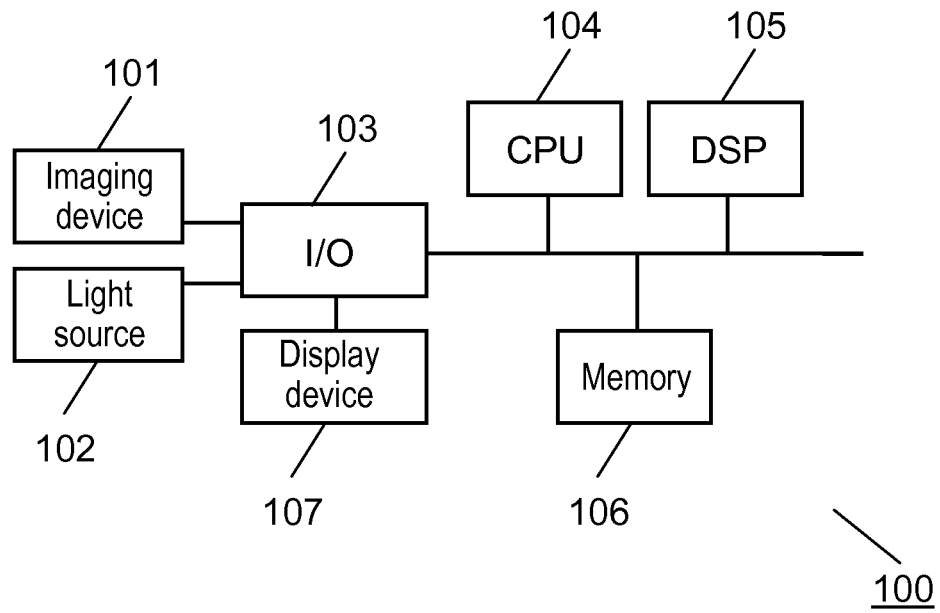
FIG. 1 is a diagram showing a hardware configuration example of an estimation apparatus in an embodiment.

Knowledge on which the Present Disclosure is Based

The inventors of the present disclosure have found out that the following problems occur in the conventional technology.

In recent years, a technology of estimating an imaged object by image processing has been developed.

According to Object Recognition based on Near-Infrared Spectral Reflectance, General Conference 2009, The Institute of Electronics, Information and Communication Engineers, Information/System Lecture Collection 2, 2009, p. 101, incident light is dispersed into three pieces by a prism, narrow-band band-pass filters are installed between the respective pieces of the dispersed light and imaging elements (image sensors), and the respective pieces of the dispersed light are imaged by such three imaging elements. Wavelengths of the band-pass filters are 870 nm, 970 nm and 1050 nm. When a pixel value of a pixel (x, y) imaged by the imaging element having the band-bass filter of a wavelength of 870 nm is i(x, y), a pixel value of a pixel (x, y) imaged by the imaging element having the band-bass filter of a wavelength of 970 nm is j(x, y), and a pixel value of a pixel (x, y) imaged by the imaging element having the band-bass filter of a wavelength of 1050 nm is k(x, y), relative reflectivity f1(x, y) and relative reflectivity f2(x, y) defined by the following expressions:

$$f1(x,y)=i(x,y)/j(x,y)$$

$$f2(x,y)=k(x,y)/j(x,y)$$

are obtained. Depending on a material, a deviation is observed in distributions of feature quantities represented by f1 and f2, and accordingly, by using this, estimation of the object such as asphalt, plant, sky and clothes is performed.

As described above, in Object Recognition based on Near-Infrared Spectral Reflectance, General Conference 2009, The Institute of Electronics, Information and Communication Engineers, Information/System Lecture Collection 2, 2009, p. 101, the estimation of the object is implemented by using infrared light.

However, in the device shown in Object Recognition based on Near-Infrared Spectral Reflectance, General Conference 2009, The Institute of Electronics, Information and Communication Engineers, Information/System Lecture Collection 2, 2009, p. 101, the prism, the band-pass filters and the three imaging elements are required. The fact that a plurality of infrared light sources (different in wavelength) are required and the fact that the prism, the band-pass filters and the three imaging elements are required cause a size increase of an device.

In order to solve such a problem as described above, an estimation apparatus according to an aspect of the present disclosure is an estimation apparatus using reflected light of infrared light reflected on an object, the estimation apparatus including: a single image sensor including a first pixel having first spectral sensitivity characteristics in a wavelength range of the infrared light and a second pixel having second spectral sensitivity characteristics different from the first spectral sensitivity characteristics in a wavelength range of the infrared light; and an estimator that estimates at least either one of a color or a material of the object based on a first output value that is an output value of the reflected light from the first pixel and based on a second output value that is an output value of the reflected light from the second pixel.

In this way, at least either one of the color or the material of the object can be estimated by using the single image sensor. That is to say, at least either one of the color or the material of the object can be estimated without causing the size increase of the device.

Moreover, for example, a single infrared light source that emits the infrared light may be included.

In this way, at least either one of the color or the material of the object can be estimated without causing the size increase of the device.

Furthermore, for example, the first spectral sensitivity characteristics may be increased when the wavelength of the infrared light becomes longer, and the second spectral sensitivity characteristics may be decreased when the wavelength of the infrared light becomes longer.

In this way, at least either one of the color or the material of the object can be estimated by the single image sensor and the single infrared light source.

Moreover, for example, the estimation apparatus may further include: data indicating a color and material of the object, the data corresponding to a ratio between the first output value and the second output value; and a ratio calculator that calculates the ratio between the first output value and the second output value, and the estimator may estimate at least either one of the color or the material of the object based on the calculated ratio and the data.

In this way, in an event of the estimation, variations among the output values of the respective pixels, which are caused by distances among the light source, the object and the image sensor, can be absorbed.

Moreover, for example, the image sensor may have a Bayer structure, the first pixel may include an optical color filter that allows transmission of blue color light, and the second pixel may include an optical color filter allowing transmission of red color light.

In this way, at least either one of the color or the material of the object can be estimated without causing the size increase of the device.

Moreover, for example, the estimation apparatus may further include a band-pass filter that allows transmission of infrared light in a specific wavelength range.

In this way, an influence of disturbance light can be reduced.

Moreover, for example, the estimation apparatus may further include a first infrared light source and a second infrared light source, the infrared light may be first infrared light emitted from the first infrared light source, the reflected light may be first reflected light, second infrared light may be emitted from the second infrared light source, and a wavelength at which illuminance of the first infrared light becomes maximum and a wavelength at which illuminance of the second infrared light becomes maximum may be different from each other.

Moreover, for example, the estimation apparatus may further include a ratio calculator that calculates a first ratio and a second ratio, and the estimator may estimate at least either one of the color or the material of the object based on the first ratio and the second ratio, the first ratio may be the ratio between the first output value and the second output value, the first pixel may have third spectral sensitivity characteristics in a wavelength range of the second infrared light, the second pixel may have fourth spectral sensitivity characteristics in a wavelength range of the second infrared light, the third spectral sensitivity characteristics may be different from the fourth spectral sensitivity characteristics, and the second ratio may be a ratio between a third output value and a fourth output value, the first pixel receives a second reflected light and outputs the third output value, the second pixel receives the second reflected light and outputs the fourth output value, and the second reflected light is a resultant of the reflection of the second infrared light on the object.

In this way, accuracy of estimating at least either one of the color or the material of the object can be enhanced.

Moreover, for example, a center emission wavelength of the first infrared light source may be 870 nm, a center emission wavelength of the second infrared light source may be 950 nm, and the object as an estimation target may be human skin.

In this way, accuracy of estimating the human skin can be enhanced.

Note that these general or specific aspects may be implemented by a method, a system, an integrated circuit, a computer program, and a computer-readable recording medium such as a CD-ROM, or may be implemented by arbitrary combinations of the method, the system, the integrated circuit, the computer program and the recording medium.

A description is specifically made below of an embodiment according to the present disclosure while referring to the drawings.

Note that the embodiment, which will be described below, shows a comprehensive or specific example in any aspect. Numeric values, shapes, materials, constituent elements, arranged positions and connection forms of the constituent elements, steps, the order of the steps shown in the embodiment are merely examples, and are not for limiting the present disclosure. Moreover, among the constituent elements in the following embodiment, constituent elements not described in independent claims showing highest-order concepts are described as arbitrary constituent elements.

Moreover, in the following description, the same reference numerals are assigned to the same constituent elements.

Names and functions of these are also the same. Hence, in some case, a detailed description of these is omitted.

EMBODIMENT

FIG. 1 is a diagram showing a hardware configuration example of an estimation apparatus of this embodiment. Estimation apparatus 100 includes: imaging device 101 such as an image sensor that images an infrared image; light source 102 such as infrared lighting such as an LED (Light Emitting Diode) that emits infrared rays with a specific wavelength; I/O (Input/Output) 103 that connects external input/output such as a camera and a display; CPU (Central Processing Unit) 104 that controls an entire system; DSP (Digital Signal Processor) 105 that mainly performs signal processing such as image processing; memory 106; and display device 107 that displays results. Note that imaging device 101 may include a visible light cut filter for suppressing an influence of visible light. In a case where imaging device 101 includes the visible light cut filter, the influence of disturbance due to visible light is reduced, and accordingly, it becomes possible to operate estimation apparatus 100 successfully even in bright environment. In FIG. 1, the estimation of at least either one of the color or the material of the object is implemented by cooperation between CPU 104 and DSP 105 or by either thereof. Note that, in order to reduce a processing load of estimation processing, the estimation processing may be implemented by using, for example, a dedicated ASIC (Application Specific Integrated Circuit), or an FPGA (Field Programmable Gate Array) as a rewritable hardware device.

Figure 2:
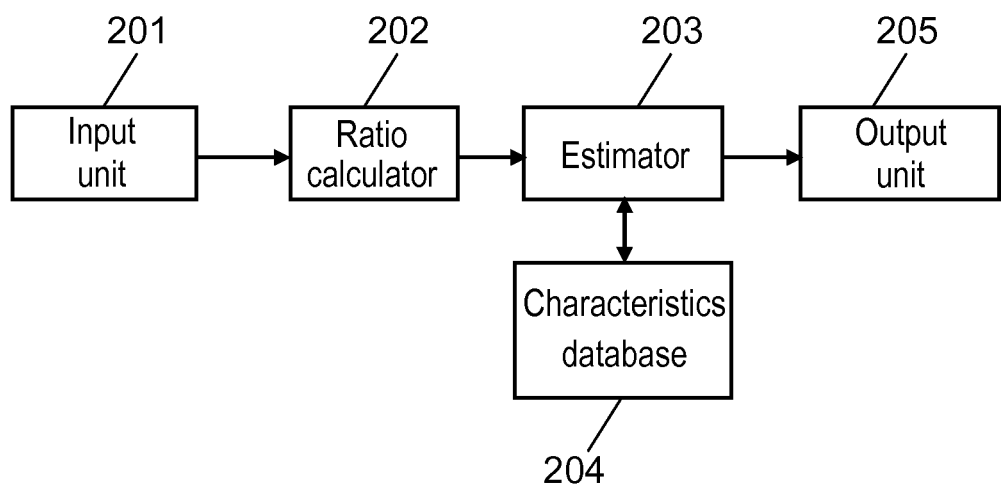
FIG. 2 is a block diagram showing a functional configuration example of the estimation apparatus in the embodiment.

FIG. 2 is a block diagram showing a functional configuration example of the estimation apparatus in this embodiment. A correspondence relationship with FIG. 1 is shown as follows.

Input unit 201 includes imaging device 101 and I/O 103.

Ratio calculator 202 and estimator 203 include programs to be executed in CPU 104 or DSP 105.

Characteristics database 204 includes data recorded in memory 106.

Output unit 205 includes display device 107 connected to I/O 103.

Estimation apparatus 100 may estimate at least either one of the color or the material of the object imaged from the infrared image input thereto, and may present a result to a user by, for example, text data, sound, a marker, coloring to the infrared image, or a change in a signal level of the infrared image. The processing will be described below in detail.

<Spectral Sensitivity Characteristics of Imaging Device>

Figure 3:
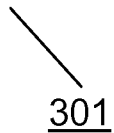
FIG. 3 is a configuration diagram of a color image sensor with a Bayer array in the embodiment.

Imaging device 101 may be a color image sensor with a Bayer array. FIG. 3 is a configuration diagram of color image sensor 301 with the Bayer array. In color image sensor 301 with the Bayer array, pixels each of which has intense sensitivity to any of red color, green color and blue color are arranged regularly. One R pixel exhibiting intense sensitivity to red light, one B pixel exhibiting intense sensitivity to blue light, and two G pixels exhibiting intense sensitivity to green light are included in 2×2 pixels. The G pixels are included one by one in a horizontal direction and vertical direction of the 2×2 pixels. In FIG. 3, each R denotes the R pixel, each B denotes the B pixel, and each G denotes the G pixel. The sensitivity of the R pixels, the sensitivity of the G pixels and the sensitivity of the B pixels are adjusted by color filters arranged in the respective pixels, and for example, the color filters have spectral sensitivity characteristics as shown in FIG. 4.

Figure 4:
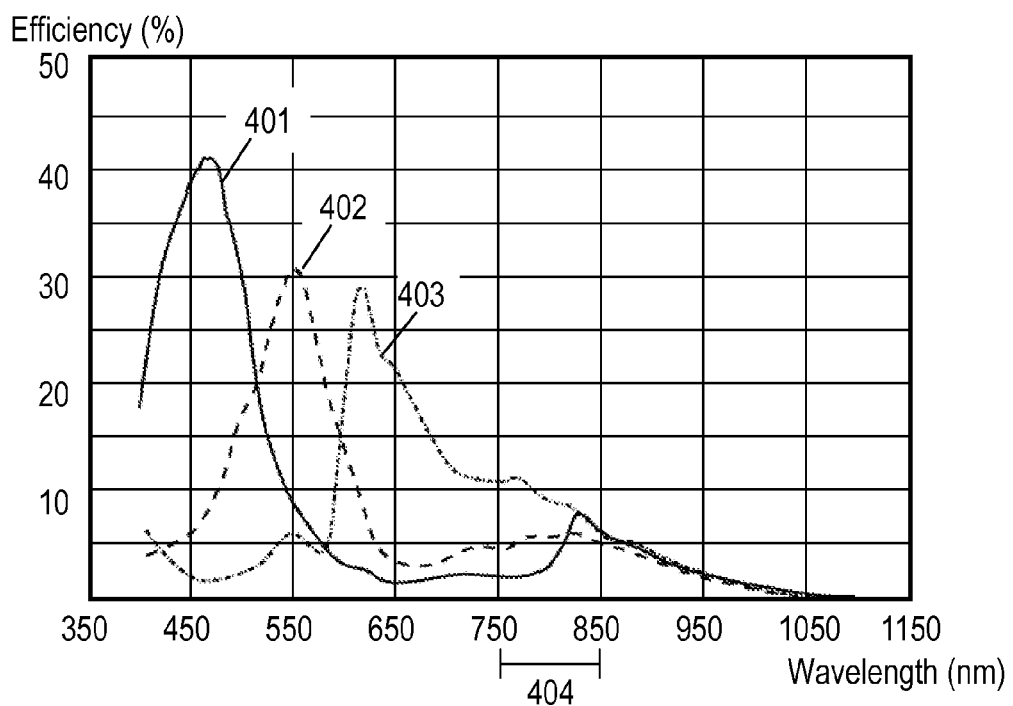
FIG. 4 is an explanatory diagram of spectral sensitivity characteristics of the color image sensor in the embodiment.

FIG. 4 shows spectral sensitivity characteristics 401 of the color filters provided in the B pixels, spectral sensitivity characteristics 402 of the color filters provided in the G pixels, and spectral sensitivity characteristics 403 of the color filters provided in the R pixels. The right side from a wavelength of 750 nm corresponds to a near-infrared region, and wavelengths of this region are used in this embodiment. Wavelength range 404 of FIG. 4 ranges from 750 nm to 850 nm. In this wavelength range 404, spectral sensitivity characteristics of the color filters provided in the B pixels, spectral sensitivity characteristics of the color filters provided in the G pixels, and spectral sensitivity characteristics of the color filters provided in the R pixels are different from one another. In particular, at around 750 nm to 850 nm, the spectral sensitivity characteristics of the color filters provided in the B pixels are largely different from the spectral sensitivity characteristics of the color filters provided in the R pixels. At around 750 nm to 850 nm, the spectral sensitivity characteristics of the color filters provided in the B pixels tend to be increased, and the spectral sensitivity characteristics of the color filters provided in the R pixels tend to be decreased. A difference among the spectral sensitivity characteristics of the respective color filters in the wavelength range of 750 nm to 850 nm is used in this embodiment.

The color image sensor exhibits intense sensitivity to the primary color (red, green, and blue) light in this embodiment. However, an important thing is the spectral sensitivity characteristics in the infrared region. Accordingly, even if the color image sensor is a color image sensor that exhibits intense sensitivity to light of complementary colors (cyan, magenta, and yellow) or is a color image sensor that exhibits intense sensitivity to light of other colors, effects similar to those in this embodiment can be expected. In order to obtain the similar effects, at least two pixels having different spectral sensitivity characteristics in a specific wavelength range just need to be arranged.

Figure 8:
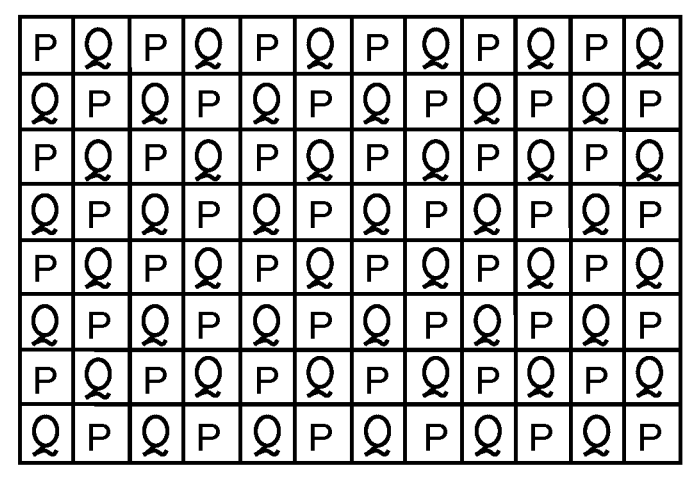

FIG. 8 is a diagram showing an example of the array of the image sensor having P pixels and Q pixels different in spectral sensitivity characteristics in the infrared range. In FIG. 8, each P denotes the P pixel, and each Q denotes the Q pixel. Even with such a configuration, it can be expected that the effects similar to those in this embodiment are obtained.

In this embodiment, the characteristics of the color filters in the wavelength range of 750 nm to 850 nm are used. However, if the color filters are configured so as to have the different spectral sensitivity characteristics, for example, in a range of 850 nm to 950 nm, then such a wavelength range of 850 nm to 950 nm can also be used. In this case, materials that have spectral reflection characteristics which are characteristic in the range of 850 nm to 950 nm can be estimated successfully. In the case where the estimation processing in this range of 850 nm to 950 nm is performed, for example, the human skin, the clothes and the hair can be estimated successfully.

<Spectral Illuminance Characteristics of Infrared LED>

Figure 5:
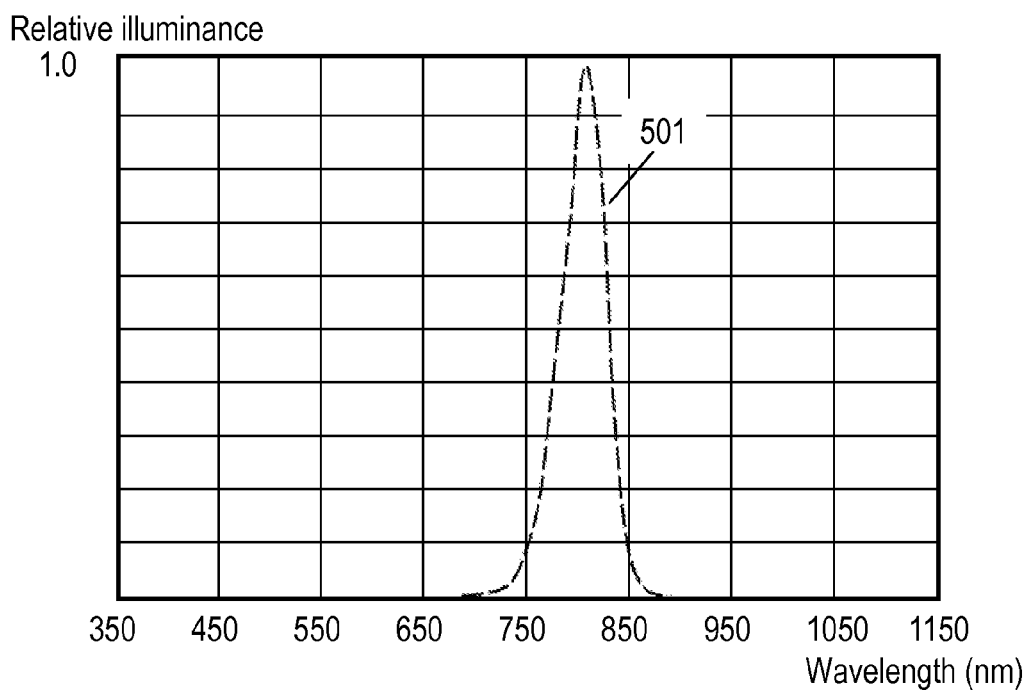
FIG. 5 is an explanatory diagram of illuminance characteristics of an infrared LED in the embodiment.

FIG. 5 shows illuminance characteristics 501 of the infrared LED, in which a wavelength of 830 nm is taken as a center. A general light source has some wavelength width as shown in FIG. 5 even if the light source is defined to be a light source with a specific wavelength. In the example of FIG. 5, the infrared LED has a wavelength width of approximately ±50 nm as a result that the illuminance gently drops from the wavelength of 830 nm taken as the center. As described above, the infrared LED light source itself irradiates infrared rays having a wavelength range with a fixed width.

In this embodiment, such a feature of the infrared light source that has a fixed width of the wavelength is used. In this embodiment, the infrared LED is illustrated as the light source. However, other infrared light sources may be used as long as the light source has a fixed wavelength width. Moreover, band-pass filters may be provided on the color image sensor side, and only infrared light within a specific wavelength range, that is, only light having a wavelength with a fixed width may be allowed to transmit therethrough. In this way, the output value from each pixel of the color image sensor can reduce the influence of disturbance light.

<Spectral Reflection Characteristics of Object>

Figure 6:
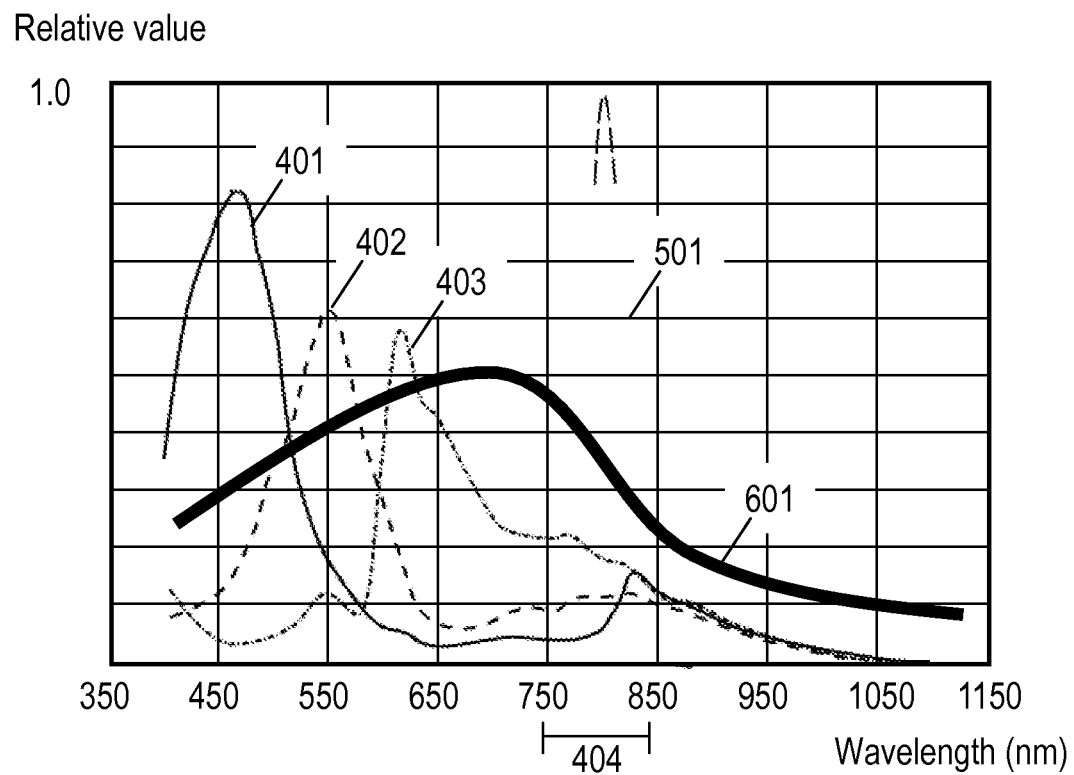
FIG. 6 is an explanatory diagram of spectral reflection characteristics and the like of a sample object in the embodiment.

FIG. 6 includes spectral reflection characteristics 601 of a sample object. Moreover, FIG. 6 includes spectral sensitivity characteristics 401 of the color filters provided in the B pixels, which are shown in FIG. 4, spectral sensitivity characteristics 402 of the color filters provided in the G pixels, which are shown in FIG. 4, spectral sensitivity characteristics 403 of the color filters provided in the R pixels, which are shown in FIG. 4, and illuminance characteristics 501 of the infrared LED, which are shown in FIG. 5. As shown by spectral reflection characteristics 601, this object has characteristics that reflectivity thereof is decreased in the range of 750 nm to 850 nm. When the infrared light that exhibits illuminance characteristics 501 of the infrared LED is irradiated onto this object, the object reflects this infrared light in accordance with spectral reflection characteristics 601. From each of the B pixels which have received the reflected light, an output that is in accordance with spectral sensitivity characteristics 401 of the color filter provided in the B pixel is obtained. From each of the G pixels which have received the reflected light, an output that is in accordance with spectral sensitivity characteristics 402 of the color filter provided in the G pixel is obtained. From each of the R pixels which have received the reflected light, an output that is in accordance with spectral sensitivity characteristics 403 of the color filter provided in the R pixel is obtained. At this time, spectral sensitivity characteristics 401 in the range of 750 nm to 850 nm in the color filter provided in the B pixel, spectral sensitivity characteristics 402 in the range of 750 nm to 850 nm in the color filter provided in the G pixel, and spectral sensitivity characteristics 403 in the range of 750 nm to 850 nm in the color filter provided in the R pixel are different from one another. Accordingly, the output value from the B pixel, the output value from the G pixel and the output value from the R pixel become different values. By using this difference in the spectral sensitivity characteristics among the B pixel, the G pixel and the R pixel, a gradient of the spectral reflection characteristics of the object in wavelength range 404 is estimated.

FIG. 7A, FIG. 7B, FIG. 7C and FIG. 7D are diagrams showing estimation examples of the gradient of the spectral sensitivity characteristics of the object. In FIG. 7A, FIG. 7B, FIG. 7C and FIG. 7D, for the sake of simplification, the following spectral sensitivity characteristics are expressed linearly, which are: spectral sensitivity characteristics 1011 of the R pixel that exhibits the intense sensitivity to the red light; spectral sensitivity characteristics 1012 of the B pixel that exhibits the intense sensitivity to the blue light; spectral sensitivity characteristics 1013 of an X pixel that exhibits the intense sensitivity to a specific color X; spectral reflection characteristics 1601 of the object; and spectral reflection characteristics 1602 of the object. However, it is not necessary that these characteristics be linear. Moreover, the illuminance characteristics of the infrared LED that serves illumination light are described here on the assumption of not depending on the wavelength; however, similar effects can be expected even in the case where the illuminance characteristics of the infrared LED are added.

Figure 7A:
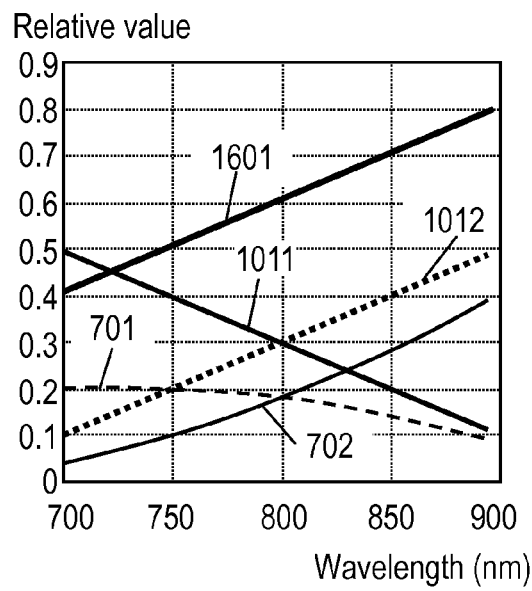
FIG. 7A is an explanatory diagram of an estimation example of a gradient of the spectral sensitivity characteristics of the object in the embodiment.
Figure 7B:
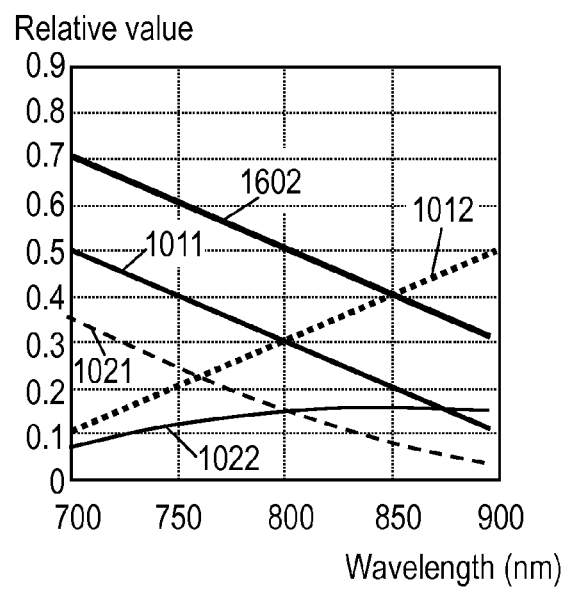
FIG. 7B is an explanatory diagram of an estimation example of the gradient of the spectral sensitivity characteristics of the object in the embodiment.

An example of estimating the gradient of the spectral reflection characteristics of the object is described by using FIG. 7A that shows an example where the spectral reflection characteristics of the object are increased monotonously in a specific wavelength range and by using FIG. 7B that shows an example where the spectral reflection characteristics of the object are decreased monotonously in the specific wavelength range.

FIG. 7A shows spectral reflection characteristics 1601 of the object, spectral sensitivity characteristics 1011 of the R pixel, spectral sensitivity characteristics 1012 of the B pixel, output characteristics 701 of the R pixel, and output characteristics 702 of the B pixel. It is assumed that, in the wavelength range of 750 nm to 850 nm, spectral sensitivity characteristics 1011 of the R pixel are decreased monotonously, and spectral sensitivity characteristics 1012 of the B pixel are increased monotonously. Moreover, it is assumed that spectral reflection characteristics 1601 of the object are increased monotonously. Output characteristics 701 of the R pixel are those in which spectral reflection characteristics 1601 of the object and spectral sensitivity characteristics 1011 of the R pixel are taken into consideration. Output characteristics 702 of the B pixel are those in which spectral reflection characteristics 1601 of the object and spectral sensitivity characteristics 1012 of the B pixel are taken into consideration. At this time, the output value of the R pixel with respect to the band of 750 nm to 850 nm is one obtained by integrating output characteristics 701 of the R pixel by such a section of 750 nm to 850 nm. In a similar way, the output value of the B pixel with respect to the band of 750 nm to 850 nm is one obtained by integrating output characteristics 702 of the B pixel by the section of 750 nm to 850 nm. As obvious from the drawing, an integrated value of output characteristics 702 of the B pixel in the section of 750 nm to 850 nm is larger than an integrated value of output characteristics 701 of the R pixel in the section of 750 nm to 850 nm.

FIG. 7B shows spectral reflection characteristics 1602 of the object, spectral sensitivity characteristics 1011 of the R pixel, spectral sensitivity characteristics 1012 of the B pixel, output characteristics 1021 of the R pixel, and output characteristics 1022 of the B pixel. It is assumed that, in the wavelength range of 750 nm to 850 nm, spectral sensitivity characteristics 1011 of the R pixel are decreased monotonously, and spectral sensitivity characteristics 1012 of the B pixel are increased monotonously. Moreover, it is assumed that spectral reflection characteristics 1602 of the object are decreased monotonously. Output characteristics 1021 of the R pixel are those in which spectral reflection characteristics 1602 of the object and spectral sensitivity characteristics 1011 of the R pixel are taken into consideration. Output characteristics 1022 of the B pixel are those in which spectral reflection characteristics 1602 of the object and spectral sensitivity characteristics 1012 of the B pixel are taken into consideration. At this time, the output value of the R pixel with respect to the band of 750 nm to 850 nm is one obtained by integrating output characteristics 1021 of the R pixel by the section of 750 nm to 850 nm. In a similar way, the output value of the B pixel with respect to the band of 750 nm to 850 nm is one obtained by integrating output characteristics 1022 of the B pixel by the section of 750 nm to 850 nm. As obvious from the drawing, an integrated value of output characteristics 1022 of the B pixel in the section of 750 nm to 850 nm is smaller than an integrated value of output characteristics 1021 of the R pixel in the section of 750 nm to 850 nm.

As described above, based on a magnitude relationship between the output value of the R pixel and the output value of the B pixel in the image sensor, it can be estimated whether the spectral reflection characteristics of the object are in an increase direction or a decrease direction with respect to a specific infrared range.

Figure 7C:
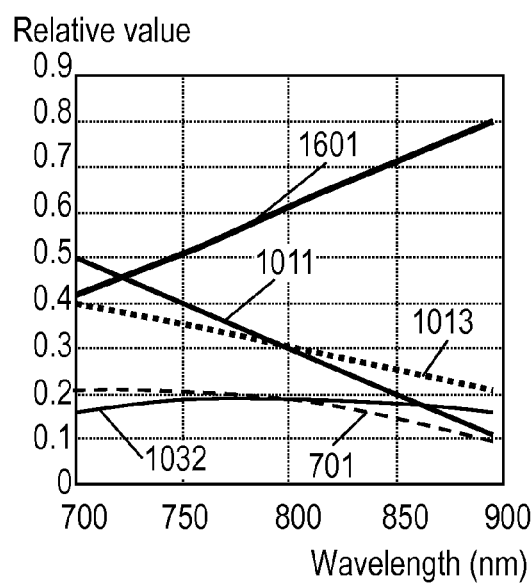
FIG. 7C is an explanatory diagram of an estimation example of the gradient of the spectral sensitivity characteristics of the object in the embodiment.

FIG. 7C shows spectral reflection characteristics 1601 of the object, spectral sensitivity characteristics 1011 of the R pixel, spectral sensitivity characteristics 1013 of the X pixel, output characteristics 701 of the R pixel, and output characteristics 1032 of the X pixel.

Figure 7D:
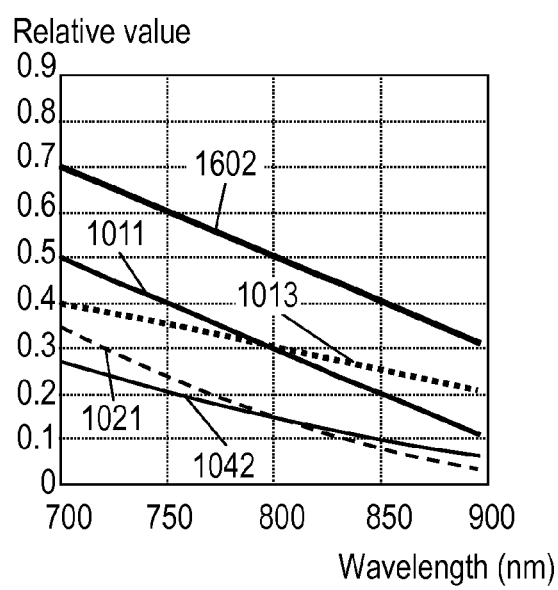
FIG. 7D is an explanatory diagram of an estimation example of the gradient of the spectral sensitivity characteristics of the object in the embodiment.

FIG. 7D shows spectral reflection characteristics 1602 of the object, spectral sensitivity characteristics 1011 of the R pixel, spectral sensitivity characteristics 1013 of the X pixel, output characteristics 1021 of the R pixel, and output characteristics 1042 of the X pixel.

Even if both of the spectral sensitivity characteristics of the sensors are decreased monotonously as shown in FIG. 7C and FIG. 7D, the spectral sensitivity characteristics are compared with each other by using the values of the respective pixels, whereby it is possible to estimate the spectral reflection characteristics of the object.

Moreover, though a description is not made here by taking an example, it is obvious that, even if both of the spectral sensitivity characteristics of the sensors are increased monotonously, it is possible to estimate the spectral reflection characteristics of the object by comparing the values of the respective pixels with one another.

As described above, at least if the spectral sensitivity characteristics of the color filters of two types of the pixels provided in the image sensor are different from each other, then the spectral reflection characteristics of the object can be estimated based on such a difference. Then, if a correspondence table between the spectral reflection characteristics and the color and the material of the object is created in advance, it is possible to estimate at least either one of the color or the material of the object by using the estimated spectral reflection characteristics and the correspondence table. Note that, as shown in FIG. 7A and FIG. 7B, desirably, the spectral sensitivity characteristics of the two types of such image sensors for use are different from each other so that the spectral sensitivity characteristics of one of the image sensors are in the increase direction with respect to the wavelength, and that the spectral sensitivity characteristics of the other image sensor can be in the decrease direction with respect to the wavelength. However, even if both of the spectral sensitivity characteristics of the two types of image sensors for use are in the decrease direction with respect to the wavelength as shown in FIG. 7C and FIG. 7D, it is possible to estimate the spectral sensitivity characteristics if the gradients of the spectral sensitivity characteristics are different from each other.

Moreover, though not shown, even if both of the spectral sensitivity characteristics of the two types of image sensors for use tend to be increased with respect to the wavelength, it is possible to estimate the spectral sensitivity characteristics if the gradients of the spectral sensitivity characteristics are different from each other.

Moreover, though only the pixel values of two pixel types (R pixel and B pixel or R pixel and X pixel) are used in this example, it is possible to estimate the spectral sensitivity characteristics more accurately by using pixel values of three pixel types (for example, R pixel, B pixel and G pixel). Furthermore, though it is described that the output values of the pixels are compared with each other in terms of the magnitude relationship in the above-described example, at least either one of the color or the material of the object may be estimated based on such a ratio as (R pixel output value)/(G pixel output value), (R pixel output value)/(B pixel output value), and (B pixel output value)/(G pixel output value). Light receiving intensity in each pixel is varied owing to distances between the light source, the object and the image sensors. However, the spectral sensitivity characteristics are estimated based on the ratio, whereby such variations of the output value of each pixel caused by variations of the distances can be absorbed in the event of the estimation.

Note that, in this embodiment, the description is made by taking as an example the color image sensor that exhibits intense sensitivity to the light of the primary colors (red, green, and blue). However, even if the color image sensor is a color image sensor that exhibits intense sensitivity to the light of the complementary colors (cyan, magenta, and yellow), the estimation can be made in a similar way to this embodiment if the spectral sensitivity characteristics of two types of the pixels have such characteristics equivalent to those described above in the infrared range that the spectral sensitivity characteristics concerned are different from each other in terms of such a value change direction. As described above, the filter characteristics of the general image sensor are used, or the characteristics thereof in the infrared wavelength range are modified, whereby the estimation of at least either one of the color or the material of the object by the single infrared light source can be implemented.

<Processing Flow>

Figure 9:
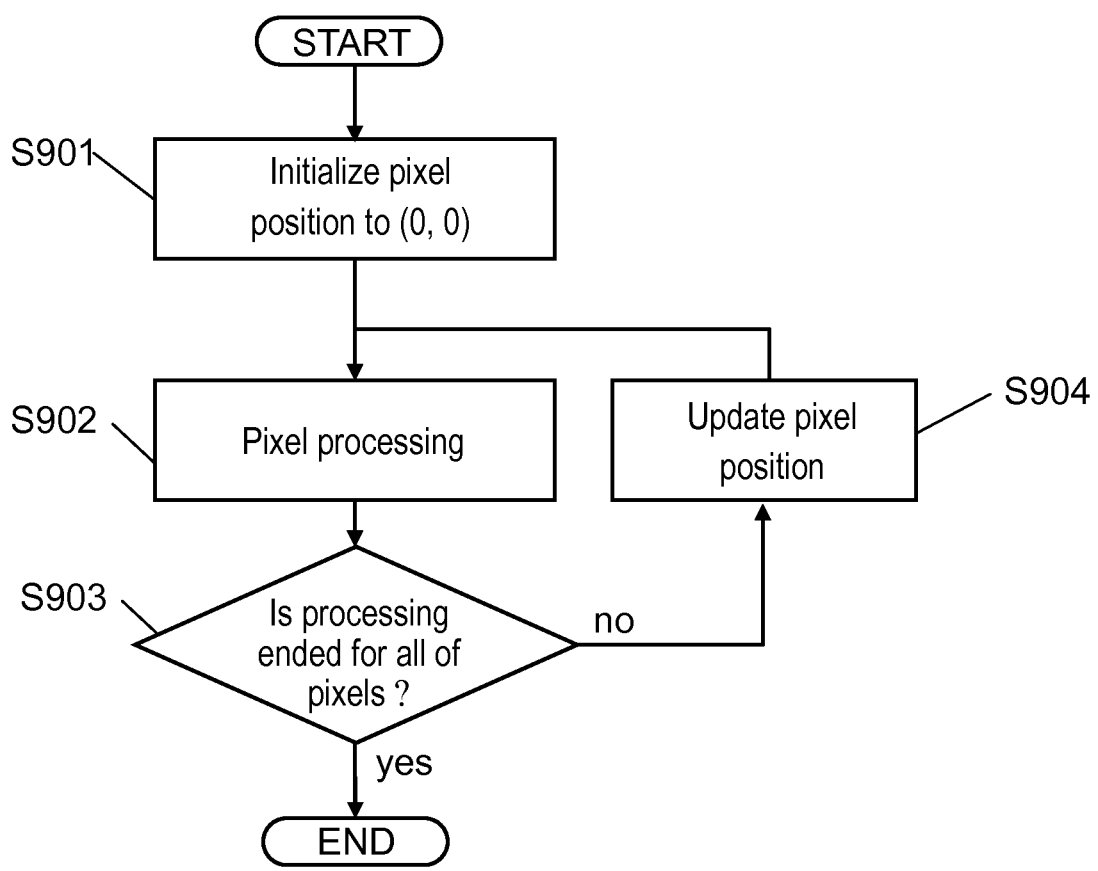
FIG. 9 is a flowchart showing an example of estimation processing in the embodiment.

A description is made of a processing flow. FIG. 9 is a flowchart showing an example of estimation processing of this embodiment.

First, coordinates of a pixel of interest are initialized to (0, 0) (S901).

Next, pixel processing for a pixel position is performed, and a result for a pixel at the pixel position is outputted (S902).

It is checked whether or not the processing is completed for all of the pixels (S903), and the processing is ended in a case where the processing is completed for all of the pixels.

Moreover, in a case where pixels to be processed remain, the position of the pixel of interest is updated, and the processing of S902 is repeated (S904).

Figure 10:
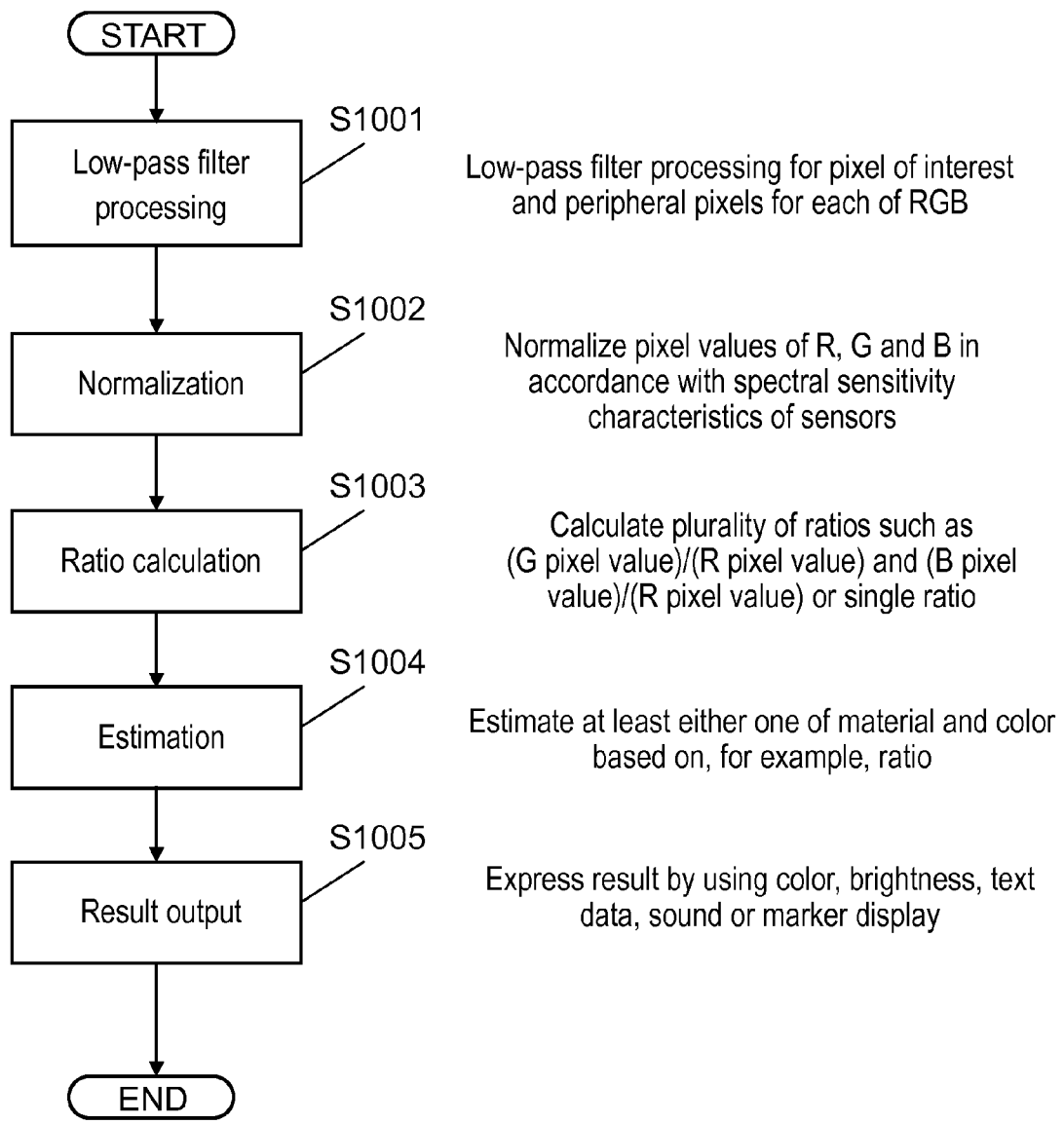
FIG. 10 is a flowchart showing an example of pixel processing in the embodiment.

FIG. 10 is a flowchart showing an example of the pixel processing S902.

In the pixel processing, first, by using pixels on a periphery of the pixel of interest, low-pass filter processing is individually performed for the output of the R pixel, the output of the G pixel and the output of the B pixel (S1001). This low-pass filter processing is processing for suppressing an influence of noise on the image, and is capable of being omitted in a case where sufficient illuminance is obtained and the influence of the noise is small.

Next, normalization processing for results of the low-pass filter processing is performed (S1002). The normalization processing is processing for correcting differences among spectral sensitivity of the R pixel, spectral sensitivity of the G pixel and spectral sensitivity of the B pixel. This normalization equalizes the spectral sensitivity of the R pixel, the spectral sensitivity of the G pixel and the spectral sensitivity of the B pixel to one another in a case where it is assumed that the spectral reflection characteristics of the object in the specific wavelength range do not depend on the wavelength. For example, this normalization can be implemented by a method to be described below.

First, in an event of manufacturing estimation apparatus 100, reference light is irradiated onto imaging device 101, and outputs of the respective pixels are obtained. Then, a lookup table, which shows a list of correction values for correcting deviations of such output values from a reference value, is created. The created lookup table is held in memory 106. Then, at a time when at least either one of the color or the material of the object is estimated, correction values corresponding to the output values of the respective pixels are obtained with reference to the created lookup table, and the output values of the respective pixels are corrected by the correction values.

Note that this normalization processing is not performed in the examples of FIG. 7A, FIG. 7B, FIG. 7C and FIG. 7D. A reason for this is as follows. Specifically, for example, in a case of the spectral sensitivity characteristics shown in FIG. 7A and FIG. 7B, the output value of the R pixel with respect to the object having the spectral reflection characteristics which do not depend on the wavelength and the output value of the B pixel with respect thereto are substantially the same, and an influence of a sensitivity difference is small. As described above, in a case where the influence of the sensitivity difference is small, it is possible to skip the normalization processing.

Next, a ratio among the output value of the R pixel, the output value of the G pixel and the output value of the B pixel is calculated (S1003). As results of this ratio calculation, for example, there are considered: one such as only (output value of R pixel)/(output value of G pixel), only (output value of R pixel)/(output value of B pixel), and only (output value of B pixel)/(output value of G pixel); and one in which two or more of these are combined with one another.

In the estimation processing, by using such a ratio, at least either one of the color or the material of the object is estimated (S1004). For the estimation of at least either one of the color or the material of the object, there are: a method of obtaining a result of the estimation by magnitude comparison such that whether the ratio is larger or smaller than 1; a method of making the estimation with reference to a table prepared in characteristics database 204 in advance; and the like. The method using the table will be described later.

In output result processing (S1005), based on the result of the estimation, the result is outputted in such ways that the pixels are colored, values of the pixels are changed (for example, such that pixels other than pixels on which a material of a specific object is present are not displayed), text data showing the result is displayed, or a portion concerned is emphasized by a marker. For example, in a case where the pixels are colored, the infrared image is color-displayed based on the result of the estimation.

Note that characteristics database 204 may hold table 1701 prepared in advance, which is as shown in FIG. 11.

Table 1701 shows colors and materials of objects, which correspond to combinations of the ratios of the output values of the pixels, the combinations being [Ai, Bi, Ci]=[(output value of R pixel)/(output value of G pixel), (output value of G pixel)/(output value of B pixel), (output value of B pixel)/(output value of R pixel)]. Here, reference symbol i denotes the number (natural number) of combinations of the ratios included in the table. As the number of data concerned is being larger (as a value of i is being larger), the accuracy of the estimation is enhanced.

From input unit 201, with regard to the pixel of interest and the pixels on the periphery of the pixel of interest, ratio calculator 202 obtains the output values of the R pixels, the output values of the G pixels, and the output values of the B pixels. Then, for example, ratio calculator 202 calculates three ratios, that is, (output value of R pixel)/(output value of G pixel), (output value of G pixel)/(output value of B pixel), and (output value of B pixel)/(output value of R pixel).

By using, as indices, such ratio combinations calculated by ratio calculator 202, the combinations being [D, E, F]=(output value of R pixel)/(output value of G pixel), (output value of R pixel)/(output value of B pixel), (output value of B pixel)/(output value of G pixel), estimator 203 searches similar sets of the ratios from table 1701 in a fuzzy manner, and outputs, as the result of the estimation, a color and a material of an object, which correspond to a most similar combination of the ratio. Note that only the color of the object may be outputted as the result of the estimation. Moreover, only the material of the object may be outputted as the result of the estimation. In such a fuzzy search, for example, the following expression:

$$(Ai-D) \times (Ai-D) + (Bi-E) \times (Bi-E) + (Ci-F) \times (Ci-F)$$

is first calculated for all values of i. Then, a value of i in a case where a value calculated in this expression is smallest is decided (i in this case is defined as j), and the color and the material, which correspond to [Aj, Bj, Cj], are decided as the result of the estimation with reference to table 1701.

Moreover, table 1701 may hold the color in place of the color and the material, and only the estimation of the color may be made. In a case where there are a plurality of the combinations of the most similar ratios, interpolation may be made between colors corresponding thereto, and a resultant thus obtained may be defined as the result of the estimation. For example, in a case where there are two combinations of the most similar ratios, and the colors corresponding thereto are blue and red, then it may be defined that the result of the estimation is purple as an intermediate color between blue and red.

Moreover, in place of the color and the material, table 1701 may hold a probability that the material is a specific material (for example, a probability that the material is human skin), and the probability that the material is a specific material may be estimated. In a case where there are a plurality of the combinations of the most similar ratios, interpolation may be made between probabilities corresponding thereto, and a resultant thus obtained may be defined as the result of the estimation. For example, in a case where there are two combinations of the most similar ratios, and the probabilities corresponding thereto are 90% and 70%, then it may be defined that the result of the estimation is 80%.

The above-described results of the estimation may be presented to the user.

As described above, in accordance with this embodiment, it becomes possible to estimate at least either one of the color or the material of the object by only using the single infrared light source and the single image sensor.

Note that this embodiment shows the example of using only the single infrared light source and the single image sensor; however, such a case of using two infrared light sources can also be considered. In this case, a gradient of the spectral reflection characteristics of the object in a wavelength range of a first infrared light source and a gradient of the spectral reflection characteristics of the object in a wavelength range of a second infrared light source can be measured. In this case, it is possible to obtain much more information in comparison with the case of estimating the gradient of one kind of the spectral reflection characteristics of the object by using two light sources in the conventional example. In this way, the estimation accuracy can be enhanced.

Moreover, it is also possible to further increase the infrared light sources, and also in this case, it becomes possible to collect much more information in a similar way in comparison with the conventional example, and it becomes possible to enhance the estimation accuracy. A description is made below of such a case of using two infrared light sources.

Such a configuration is considered, in which a center emission wavelength (wavelength at which the illuminance becomes maximum) of the first infrared light source is set at 870 nm, a center emission wavelength (wavelength at which the illuminance becomes maximum) of the second infrared light source is set at 950 nm, and it is determined whether or not the object is the human skin.

At around the wavelength of 870 nm, the spectral reflection characteristics of the human skin are decreased when the wavelength is increased. Moreover, at around the wavelength of 950 nm, the spectral reflection characteristics of the human skin are decreased when the wavelength is increased.

It is assumed that the image sensor includes a Y pixel and a Z pixel. It is assumed that, at around the wavelength of 870 nm, spectral characteristics of the Y pixel are increased when the wavelength is increased. It is assumed that, at around the wavelength of 950 nm, spectral characteristics of the Y pixel are increased when the wavelength is increased.

Moreover, it is assumed that, at around the wavelength of 870 nm, spectral characteristics of the Z pixel are decreased when the wavelength is increased. It is assumed that, at around the wavelength of 950 nm, spectral characteristics of the Z pixel are decreased when the wavelength is increased. Moreover, it is assumed that an output of the Y pixel and an output of the Z pixel are normalized.

In the measurement, first, the first infrared light source is allowed to emit light without allowing the second infrared light source to emit light, and an output of the Y pixel that has received the reflected light from the object is defined as Y1, and an output of the Z pixel that has received the reflected light therefrom is defined as Z1. It is understood that, when Y1/Z1 is smaller than 1, the spectral reflection characteristics of the object are decreased when the wavelength is increased at around 870 nm. This determination is defined as a first determination.

Next, the second infrared light source is allowed to emit light without allowing the first infrared light source to emit light, and an output of the Y pixel that has received the reflected light from the object is defined as Y2, and an output of the Z pixel that has received the reflected light therefrom is defined as Z2. It is understood that, when Y2/Z2 is smaller than 1, the spectral reflection characteristics of the object are decreased when the wavelength is increased at around 950 nm. This determination is defined as a second determination.

Then, when the spectral reflection characteristics of the object are decreased in the first determination, and the spectral reflection characteristics of the object in the second determination, it is determined that the object is the human skin. That is to say, the determination as to whether or not the object is the human skin is performed by using four pieces of information.

This estimation using four pieces of information has a larger information amount in comparison with estimation using two pieces of information, for example, estimation to be performed by using only a difference between a pixel value of the Y pixel imaged by using the first infrared light source and a pixel value of the Y pixel imaged by using the second infrared light source. Accordingly, the estimation accuracy is enhanced.

Other Modification Examples

As the exemplification of the technology disclosed in this application, the embodiment has been described as above. However, it is a matter of course that the technology in this disclosure is not limited to this. Such cases as below are also incorporated in this embodiment.

(1) Specifically, the present disclosure of this embodiment may be a computer system composed of a microprocessor, a ROM, a RAM, a hard disk unit, a display unit, a keyboard, a mouse and the like. A computer program is stored in the RAM or the hard disk unit. The microprocessor operates in accordance with the computer program, whereby the respective devices achieve functions thereof. Here, the computer program is composed in such a manner that a plurality of command codes indicating instructions to the computer are combined with one another in order to achieve a predetermined function.

(2) A part or all of the constituent elements which compose the above-described device may be composed of one system LSI (Large Scale Integrated Circuit). The system LSI is a super multi-functional LSI manufactured by integrating a plurality of constituent units on one chip, and specifically, is a computer system composed by including the microprocessor, the ROM, the RAM and the like. In the RAM, the computer program is stored. The microprocessor operates in accordance with the computer program, whereby the system LSI achieves a function thereof.

(3) A part or all of the constituent elements which compose the above-described device may be composed of an IC card detachable from each device or of a module as a single body. The IC card or the module is a computer system composed of the microprocessor, the ROM, the RAM and the like. The IC card or the module may include the super multi-functional LSI described above. The microprocessor operates in accordance with the computer program, whereby the IC card or the module achieves a function thereof. This IC card or this module may have tamper resistance.

(4) The present disclosure according to this embodiment may be the methods shown above. Moreover, these methods may be computer programs implemented by the computer, or may be digital signals made of the computer program.

Furthermore, the present disclosure according to this embodiment may be one in which the computer programs or the digital signals are recorded in a computer-readable recording medium, for example, such as a flexible disk, a hard disk, a CD-ROM, an MO, a DVD, a DVD-ROM, a DVD-RAM, a BD (Blue-ray (registered trademark) Disc), and a semiconductor memory. Moreover, the present disclosure may be digital signals recorded in these recording mediums.

Moreover, the present disclosure according to this embodiment may be one in which the computer programs or the digital signals are transferred via a telecommunication line, a wireless or wired communication line, a network represented by the Internet, data broadcasting and the like.

Furthermore, the present disclosure according to this embodiment may be a computer system including a microprocessor and a memory, the memory may store the above-described computer programs, and the microprocessor may operate in accordance with the computer programs.

Moreover, the programs or the digital signals are recorded in the recording medium and are transferred, or the programs or the digital signals are transferred via the network and the like, whereby the programs or the digital signals may be embodied by other independent computer systems.

(5) The above-described embodiment and the above-described modification examples may be combined with each other.

INDUSTRIAL APPLICABILITY

The estimation apparatus according to the present disclosure is useful as such a device that estimates at least either one of the color or the material of the object by using the reflected light of the infrared light reflected on the object.

What is claimed is:

1. An estimation apparatus using reflected light of infrared light reflected on an object, the estimation apparatus comprising:
   at least one infrared light source that emits the infrared light;
   a single image sensor including a first pixel having first spectral sensitivity characteristics in a wavelength range of the infrared light and a second pixel having second spectral sensitivity characteristics different from the first spectral sensitivity characteristics in the wavelength range of the infrared light; and
   an estimator that estimates data indicating at least either one of a color or a material of the object based on a first output value that is an output value of the reflected light from the first pixel and based on a second output value that is an output value of the reflected light from the second pixel, the data corresponding to a ratio between the first output value and the second output value,
   wherein the first spectral sensitivity characteristics in a wavelength range from 750 nm to 850 nm are increased when the wavelength of the infrared light becomes longer, and the second spectral sensitivity characteristics in the wavelength range from 750 nm to 850 nm are decreased when the wavelength of the infrared light becomes longer,
   a maximum value of the first spectral sensitivity characteristics in a wavelength range below 750 nm is bigger than a maximum value of the first spectral sensitivity characteristics in the wavelength range from 750 nm to 850 nm, and
   a maximum value of the second spectral sensitivity characteristics in the wavelength range below 750 nm is bigger than a maximum value of the second spectral sensitivity characteristics in the wavelength range from 750 nm to 850 nm.

2. The estimation apparatus according to claim 1, further comprising:
   a ratio calculator that calculates the ratio between the first output value and the second output value,
   wherein the estimator estimates at least either one of the color or the material of the object based on the calculated ratio and the data.

3. The estimation apparatus according to claim 2,
   wherein the image sensor has a Bayer structure,
   the first pixel includes an optical color filter that allows transmission of blue color light, and
   the second pixel includes an optical color filter allowing transmission of red color light.

4. The estimation apparatus estimator according to claim 3, further comprising:
   a band-pass filter that allows transmission of infrared light in a specific wavelength range.

5. The estimation apparatus according to claim 1, wherein:
   the at least one infrared light source includes a first infrared light source and a second infrared light source,
   wherein the infrared light is first infrared light emitted from the first infrared light source, and the reflected light is first reflected light,
   second infrared light is emitted from the second infrared light source, and
   a wavelength at which illuminance of the first infrared light becomes maximum and a wavelength at which illuminance of the second infrared light becomes maximum are different from each other.

6. The estimation apparatus according to claim 5, further comprising:
   a ratio calculator that calculates the ratio and a second ratio,
   wherein the estimator estimates at least either one of the color or the material of the object based on the ratio and the second ratio,
   the first pixel has third spectral sensitivity characteristics in a wavelength range of the second infrared light,
   the second pixel has fourth spectral sensitivity characteristics in a wavelength range of the second infrared light,
   the third spectral sensitivity characteristics are different from the fourth spectral sensitivity characteristics,
   the second ratio is a ratio between a third output value and a fourth output value,
   the first pixel receives a second reflected light and outputs the third output value,
   the second pixel receives the second reflected light and outputs the fourth output value, and
   the second reflected light is a resultant of the reflection of the second infrared light on the object.

7. The estimation apparatus according to claim 6,
   wherein a center emission wavelength of the first infrared light source is 870 nm,
   a center emission wavelength of the second infrared light source is 950 nm, and
   the object as an estimation target is human skin.

8. An estimation method using reflected light of infrared light reflected on an object, the estimation method comprising:
   emitting the infrared light by at least one infrared light source;
   receiving the reflected light by a first pixel having first spectral sensitivity characteristics in a wavelength range of the infrared light;
   outputting a first output value from the first pixel;
   receiving the reflected light by a second pixel having second spectral sensitivity characteristics different from the first spectral sensitivity characteristics in the wavelength range of the infrared light;
   outputting a second output value from the second pixel; and
   estimating data indicating at least either one of a color or a material of the object based on the first output value and the second output value, the data corresponding to a ratio between the first output value and the second output value,
   wherein the first pixel and the second pixel are included in a single image sensor,
   the first spectral sensitivity characteristics in a wavelength range from 750 nm to 850 nm are increased when the wavelength of the infrared light becomes longer, and the second spectral sensitivity characteristics in the wavelength range from 750 nm to 850 nm are decreased when the wavelength of the infrared light becomes longer,
   a maximum value of the first spectral sensitivity characteristics in a wavelength range below 750 nm is bigger than a maximum value of the first spectral sensitivity characteristics in the wavelength range from 750 nm to 850 nm, and
   a maximum value of the second spectral sensitivity characteristics in the wavelength range below 750 nm is bigger than a maximum value of the second spectral sensitivity characteristics in the wavelength range from 750 nm to 850 nm.

9. An integrated circuit for an estimation apparatus using reflected light of infrared light reflected on an object, the integrated circuit comprising:
   an estimator that estimates data indicating at least either one of a color and material of the object based on a first output value and a second output value, the data corresponding to a ratio between the first output value and the second output value, wherein at least one infrared light source emits the infrared light, a single image sensor that includes a first pixel and a second pixel outputs the first output value and the second output value, the first pixel has first spectral sensitivity characteristics in a wavelength range of the infrared light, the second pixel has second spectral sensitivity characteristics different from the first spectral sensitivity characteristics in the wavelength range of the infrared light, the first output value is an output value of the reflected light from the first pixel, the second output value is an output value of the reflected light from the second pixel, the first spectral sensitivity characteristics in a wavelength range from 750 nm to 850 nm are increased when the wavelength of the infrared light becomes longer, and the second spectral sensitivity characteristics in the wavelength range from 750 nm to 850 nm are decreased when the wavelength of the infrared light becomes longer, a maximum value of the first spectral sensitivity characteristics in a wavelength range below 750 nm is bigger than a maximum value of the first spectral sensitivity characteristics in the wavelength range from 750 nm to 850 nm, and a maximum value of the second spectral sensitivity characteristics in the wavelength range below 750 nm is bigger than a maximum value of the second spectral sensitivity characteristics in the wavelength range from 750 nm to 850 nm.

10. A non-transitory computer-readable recording medium comprising:

a program for allowing a computer to execute the estimation method according to claim 8.

* * * * *